(12) United States Patent
Gold

(10) Patent No.: US 7,282,340 B2
(45) Date of Patent: *Oct. 16, 2007

(54) METHODS FOR IDENTIFYING AN ANALOG THAT PROMOTES NERVE REGENERATION

(75) Inventor: Bruce G. Gold, West Linn, OR (US)

(73) Assignee: Oregon Health Sciences University, Portland, OR (US)

( * ) Notice: Subject to any disclaimer, the term of this patent is extended or adjusted under 35 U.S.C. 154(b) by 305 days.

This patent is subject to a terminal disclaimer.

(21) Appl. No.: 10/943,506

(22) Filed: Sep. 17, 2004

(65) Prior Publication Data

US 2005/0142533 A1     Jun. 30, 2005

Related U.S. Application Data

(63) Continuation of application No. 09/130,887, filed on Aug. 7, 1998, now Pat. No. 6,852,496.

(60) Provisional application No. 60/055,560, filed on Aug. 12, 1997.

(51) Int. Cl.
  *G01N 33/53* (2006.01)
  *A61K 31/44* (2006.01)

(52) U.S. Cl. .................. 435/7.1; 435/7.2; 514/2; 514/340

(58) Field of Classification Search .............. None
See application file for complete search history.

(56) References Cited

U.S. PATENT DOCUMENTS

| | | |
|---|---|---|
| 3,595,955 A | 7/1971 | De Boer et al. |
| 3,987,035 A | 10/1976 | Rinehart, Jr. et al. |
| 4,075,339 A | 2/1978 | Rinehart, Jr. et al. |
| 4,261,989 A | 4/1981 | Sasaki et al. |
| 5,192,773 A | 3/1993 | Armistead et al. |
| 5,330,993 A | 7/1994 | Armistead et al. |
| 5,387,584 A | 2/1995 | Schnur |
| 5,516,797 A | 5/1996 | Armistead et al. |
| 5,525,523 A | 6/1996 | Soldin |
| 5,543,423 A | 8/1996 | Zelle et al. |
| 5,612,350 A | 3/1997 | Or et al. |
| 5,614,547 A | 3/1997 | Hamilton et al. |
| 5,620,971 A | 4/1997 | Armistead et al. |
| 5,622,970 A | 4/1997 | Armistead et al. |
| 5,639,592 A | 6/1997 | Evans et al. |
| 5,665,774 A | 9/1997 | Armistead et al. |
| 5,717,092 A | 2/1998 | Armistead et al. |
| 5,780,484 A | 7/1998 | Zelle et al. |
| 5,786,378 A | 7/1998 | Hamilton et al. |
| 5,801,197 A | 9/1998 | Steiner et al. |
| 5,811,434 A | 9/1998 | Zelle et al. |
| 5,840,736 A | 11/1998 | Zelle et al. |
| 5,968,921 A | 10/1999 | Gold |
| 6,037,370 A | 3/2000 | Armistead |

FOREIGN PATENT DOCUMENTS

| | | |
|---|---|---|
| WO | WO92/04370 | 3/1992 |
| WO | WO92/19593 | 11/1992 |
| WO | WO92/19745 | 11/1992 |
| WO | WO92/21313 | 12/1992 |
| WO | WO93/07269 | 4/1993 |
| WO | WO93/14215 | 7/1993 |
| WO | WO93/23548 | 11/1993 |
| WO | WO96/40140 | 12/1996 |
| WO | WO96/40633 | 12/1996 |
| WO | WO96/41609 | 12/1996 |
| WO | WO97/18828 | 5/1997 |
| WO | WO98/20891 | 5/1998 |
| WO | WO98/20892 | 5/1998 |
| WO | WO98/20893 | 5/1998 |
| WO | WO99/21552 | 5/1999 |

OTHER PUBLICATIONS

Armistead et al., *Acta Cryst* D51:522-528, 1995.
Harding et al., *Nature* 341:758-760, 1989.
Siekierka et al., *Nature* 341:755-757, 1989.
Steiner et al., *Nature Medicine* 3:421-428, 1997.

*Primary Examiner*—Janet L. Andres
*Assistant Examiner*—Aditi Dutt
(74) *Attorney, Agent, or Firm*—Klarquist Sparkman, LLP

(57) ABSTRACT

Analogs of FK506 that do not bind FKBP-12 have been found to effectively promote nerve cell growth and regeneration, thereby speeding functional recovery of damaged nervous tissue and axonal regeneration without causing immunosuppression.

14 Claims, 10 Drawing Sheets

ND AN ANALOG
METHODS FOR IDENTIFYING AN ANALOG
THAT PROMOTES NERVE REGENERATION

PRIORITY CLAIM

This is a continuation of U.S. patent application Ser. No. 09/130,887, filed Aug. 7, 1998 now U.S. Pat. No. 6,852,496, which claims the benefit of U.S. Provisional Application No. 60/055,560, filed Aug. 12, 1997, both of which are incorporated herein by reference.

BACKGROUND OF THE INVENTION

Following traumatic or mechanically induced axonal degeneration in the peripheral nervous system, axonal regeneration ensues, resulting in functional recovery. However, the rate of axonal elongation (3-4 mm/day) is slow. Consequently, recovery is measured in weeks or months, depending upon the distance between the site of injury and the target tissue. Therapies that speed regeneration over long distances would be highly beneficial to patients and would significantly reduce health care costs.

The immunosuppressant drug FK506 (USAN tacrolimus; Prograf®) possesses a variety of neuronal properties, including protection against ischemic brain injury (Sharkey and Butcher, *Nature* 371:336-339, 1994; Ide et al., *Neurosci. Lett.* 204:157-160, 1996; Tokime et al., *Neurosci. Lett.* 206:81-84, 1996) and glutamate toxicity in vitro (Dawson et al., *Proc. Natl. Acad. Sci. USA* 90:9808-9812, 1993), prevention of N-methyl-D-aspartate (NMDA) receptor desensitization (Tong et al., *Science* 267:1510-1512, 1995), prevention of kindling (Moriwaki et al., *Neurosci. Res.* 25:191-194, 1996), blockade of long-term potentiation (LTP) and long-term depression (LTD) in the visual cortex (Torri et al., *Neuroscience* 185:1-4, 1995; Funauchi et al., *Neurosci. Res.* 19:269-278, 1994), facilitation of LTP (Ikegami et al., *Mol. Brain Res.* 41:183-191, 1996) and blockade of LTD in the rat hippocampus (Hodgkiss and Kelly, *Brain Res.* 705:241-246, 1995), and alteration in neurotransmitter release (Steiner et al., *Mol. Med.* 96:1076-1151, 1996) and endocytosis (Kuromi et al., *Neurosci. Res.* 27:101-113, 1997). It is likely that these neuronal properties of FK506 are mediated by calcineurin inhibition. FK506 also speeds functional recovery and axonal regeneration in the rat in a dose-dependent manner following a sciatic nerve crush lesion (Gold et al., *J. Neurosci.* 15:7505-7516, 1995; Gold et al., *Restor. Neurol. Neurosci.* 6:287-296, 1994). FK506 was shown to stimulate neuritic outgrowth in a rat pheochromocytoma cell line in a concentration-dependent manner (Lyons et al., *Proc. Natl Acad. Sci. USA* 91:3191-3195, 1994).

FK506 and cyclosporin A share a common mechanism for producing immunosuppression; both inhibit the protein phosphatase calcineurin following binding to their respective immunophilins, FK506-binding protein-12 (KBP-12) and cyclophilin A (Harding et al., *Nature* 341:758-760, 1989; Siekierka et al., *Nature* 341:755-757, 1989; Sigal and Dumont, *Annu. Rev. Immunol.* 10:519-560, 1992; Snyder and Sabatini, *Nature Medicine* 1:32-37, 1995; Wiederrect and Edzkorn, *Perspectives in Drug Discovery and Design* 2:57-84, 1995). It has been thought that the activity of FK506 in promoting nerve regeneration and growth is also related to the binding of FKBP-12.

There has been an intense effort to design compounds that are structurally related to FK506 and that share FK506's ability to inhibit FKBP-12 and thereby produce immunosuppression. See, for example: Bierer et al., *Science* 250:556-559, 1990; Van Duyne et al., *Science* 252:839-842, 1991; Van Duyne et al., *J. Mol. Biol.* 229:105-124, 1993; Hauske et al., *J. Med. Chem.* 35:4284-4296, 1992; Holt et al., *J. Am. Chem. Soc.* 115:9925-9938, 1993; Holt et al., *Bioorg. Med Chem. Lett.* 3:1977-1980, 1993; Teague and Stocks, *Bioorg. Med. Chem. Lett.* 3:1947-1950, 1993; Wang et al., *Bioorg. Med. Chem. Lett.* 4:1161-1166, 1994; Yamashita et al., *Bioorg. Med Chem. Lett.* 4:325-328, 1994; Stocks et al., *Bioorg. Med Chem. Lett.* 4:1457-1460, 1994; Goulet et al., *Perspect. Drug Disc. Design* 2:145-162, 1994; Wilson et al., *Acta Cryst.* D51:511-521, 1995; Armistead et al., *Acta Cryst.* D51:522-528, 1995; U.S. Pat. Nos. 5,192,773, 5,330,993, 5,516,797, 5,612,350, 5,614,547, 5,622,970, 5,654,332; and published international patent applications WO 92/00278, WO 92/04370, WO 92/19593, WO 92/21313, WO 94/07858, and WO 96/40633 (Hamilton and Steiner).

Snyder and co-workers have reported (Steiner et al., *Nature Medicine* 3:1-8, 1997; Steiner et al., *Proc. Natl. Acad. Sci. USA* 94:2019-2024, 1997) that systemic administration (via subcutaneous injection) of two such molecules that bind FKBP-12 (with binding affinities of 25 and 250 nM, respectively) but that do not inhibit calcineurin activity (and which are not immunosuppressants) increase the size of myelinated fibers.

U.S. Pat. No. 5,654,332 (Armistead et al.) discusses immunosuppressive compounds that bind FKBP-12 and that are said to stimulate neurite outgrowth in the presence of NGF. It was stated that the neurotrophic activity of these FKBP-12 binding compounds "is directly related to their affinity for FKBP-12 and their ability to inhibit FKBP-12 rotomase activity" (id. at col. 7, lines 47-50).

SUMMARY OF THE INVENTION

FK506 analogs that do not bind FKBP-12 surprisingly have neurotrophic activity, displaying effectiveness in promoting nerve regeneration and functional recovery and stimulating neuritic outgrowth, for example.

According to one embodiment of the invention, pharmaceutical compositions are provided that comprise an amount of a non-FKBP-12-binding ("non-binding") FK506 analog that is effective in stimulating nerve cell growth and a pharmaceutically acceptable excipient, for example, a composition comprising a unit dose of the non-binding FK506 analog. Such compositions can also include other active ingredients, e.g., one or more neurotrophic factors including, but not limited to, neurotrophic growth factor (NGF), insulin growth factor (IGF-1), acidic or basic fibroblast growth factor (aFGF and bFGF, respectively), platelet-derived growth factor (PDGF), brain-derived neurotrophic factor (BDNF), ciliary neurotrophic factors (CNTF), glial cell line-derived neurotrophic factor (GDNF), neurotrophin-3 (NT-3), and neurotrophin 4/5 (NT 4/5). A preferred neurotrophic compound is NGF.

According to another embodiment of the invention, therapeutic methods are provided that comprise administering to a patient a pharmaceutical composition comprising a non-binding FK506 analog. For example, such methods can include administering an amount of such a composition that is effective in stimulating nerve cell growth.

According to another embodiment of the invention, methods for stimulating neurite outgrowth are provided that comprise contacting a nerve cell with a composition comprising a neurotrophic amount of a non-binding FK506 compound.

According to another embodiment of the invention, methods of drug discovery are provided that comprise assaying FK506 analogs for binding to FKBP-12, selecting an FK506 analog that does not bind FKBP-12, and assaying the selected FK506 analog for activity in promoting nerve cell growth.

The foregoing and various features and advantages of the invention will become more apparent from the following detailed description and accompanying drawings.

BRIEF DESCRIPTION OF THE DRAWINGS

FIG. 5A: Low-power (2,000×) electron micrograph of vehicle-treated rat. FIG. 5B: Low-power (2,000×) electron micrograph of V-10,367-treated rat. FIG. 5C: High-power (4,000×) electron micrograph of vehicle-treated rat. FIG. 5D: High-power (4,000×) electron micrograph of V-10,367-treated rat. Scale bar represents 10 μm (FIGS. 5A and 5B) or 5 μm (FIGS. 5C and 5D).

DETAILED DESCRIPTION

Surprisingly, FK506 analogs that do not bind FKBP-12 have been found to effectively speed functional recovery of damaged nervous tissue and axonal regeneration. This discovery indicates that cyclophilin A-mediated calcineurin inhibition, which is dependent upon FKBP-12 binding, probably does not play a role in the ability of FK506 to speed nerve regeneration and that the nerve regenerative and immunosuppressive effects of FK506 arise via distinct mechanisms. The efficacy of FK506 and related compounds in promoting neurite outgrowth does not necessarily involve FKBP-12 inhibition.

Definitions

Figure 1:
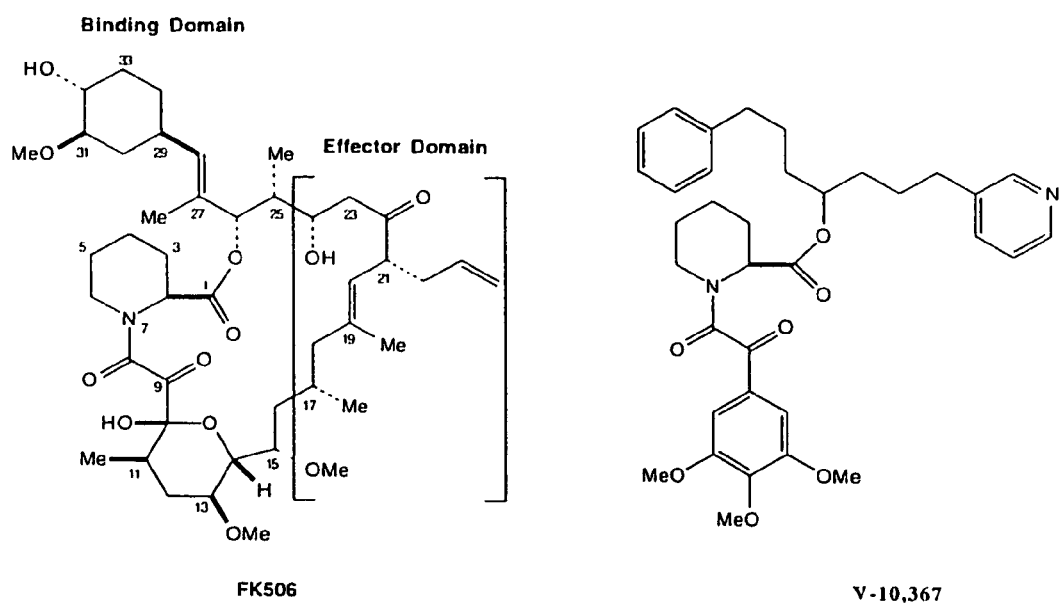
FIG. 1 shows structures of FK506 (left) and V-10,367 (right). The bracketed portion of FK506 represents the calcineurin-binding domain, which is absent in V-10,367.

"FK506 analogs" are compounds that are functionally analogous to FK506 in their ability to stimulate neuritic outgrowth. Preferably, such FK506 analogs retain the FKBP-12 binding domain but lack the structural components of the effector domain (FIG. 1). FK506 analogs include, but are not limited to:

(1) Compounds represented by the formula I (see U.S. Pat. Nos. 5,622,970, 5,516,797, 5,330,993, 5,192,773, and WO 92/00278 regarding synthesis of these compounds, the disclosures of which are incorporated herein by reference):

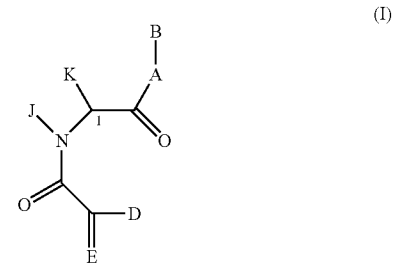

(I)

wherein A is O, NH, or N—(C1-C4 alkyl);

wherein B is hydrogen, CHL-Ar, (C1-C6)-straight or branched alkyl, (C2-C6)-straight or branched alkenyl, (C5-C7)-cycloalkyl, (C5-C7)-cycloalkenyl or Ar substituted (C1-C6)-alkyl or (C2-C6)-alkenyl, or

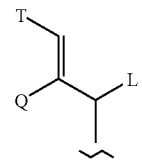

wherein L and Q are independently hydrogen, (C1-C6)-straight or branched alkyl or (C2-C6)-straight or branched alkenyl;

wherein T is Ar or substituted cyclohexyl with substituents at positions 3 and 4 that are independently selected from the group consisting of hydrogen, hydroxyl, O—(C1-C4)-alkyl or O—(C2-C4)-alkenyl and carbonyl;

wherein Ar is selected from the group consisting of 1-naphthyl, 2-naphthyl, 2-furyl, 3-furyl, 2-thienyl, 2-pyridyl, 3-pyridyl, 4-pyridyl and phenyl having one to three substituents that are independently selected from the group consisting of hydrogen, halo, hydroxyl, nitro, $CF_3$, (C1-C6)-straight or branched alkyl or (C2-C6)-straight or branched alkenyl, O—(C1-C4)-straight or branched alkyl or O—(C2-C4)-straight or branched alkenyl, O-benzyl, O-phenyl, amino and phenyl;

wherein D is U; E is either oxygen or CH-U, provided that if D is hydrogen, then E is CH—U or if E is oxygen, then D is not hydrogen;

wherein each U is independently selected from hydrogen, O—(C1-C4)-straight or branched alkyl or O—(C2-C4)-straight or branched alkenyl, (C1-C6)-straight or branched alkyl or (C2-C6)-straight or branched alkenyl, (C5-C7)-cycloalkyl or (C5-C7)-cycloalkenyl substituted with (C1-C4)-straight or branched alkyl or (C2-C4)-straight or branched alkenyl, 2-indolyl, 3-indolyl, [(C1-C4)-alkyl or (C2-C4)-alkenyl]-Ar or Ar;

wherein J is hydrogen or C1 or C2 alkyl or benzyl; K is (C1-C4)-straight or branched alkyl, benzyl or cyclohexylmethyl; or wherein J and K may be taken together to form a 5-7 membered heterocyclic ring that may contain an oxygen (O), sulfur (S), SO or $SO_2$ substituent therein; and the stereochemistry at position 1 is R or S.

(2) Compounds represented by the formula II (see U.S. Pat. No. 5,654,332, WO 94/07858, and WO 92/19593 for synthesis of these compounds, the disclosures of which are incorporated herein by reference):

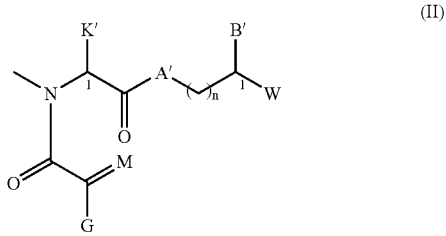

(II)

wherein A' is $CH_2$, oxygen, NH, or N—(C1-C4 alkyl);

wherein B' and W are independently hydrogen, Ar', (C1-C10)-straight or branched alkyl, (C2-C10)-straight or branched alkenyl or alkynyl, (C5-C7)-cycloalkyl substituted (C1-C6)-straight or branched alkyl, (C2-C6)-straight or branched alkenyl or alkynyl, (C5-C7)-cycloalkenyl substituted (C1-C6)-straight or branched alkyl, (C2-C6)-straight or branched alkenyl or alkynyl, or Ar' substituted (C1-C6)-straight or branched alkyl, (C2-C6)-straight or branched alkenyl or alkynyl wherein in each case, any one of the $CH_2$ groups of the alkyl, alkenyl, or alkynyl chains may be optionally replaced by a heteroatom selected from the group consisting of O, S, SO, $SO_2$, N, and NR, wherein R is selected from the group consisting of hydrogen, (C1-C4)-straight or branched alkyl, (C2-C4)-straight or branched alkenyl or alkynyl, and (C1-C4) bridging alkyl wherein a bridge is formed between the nitrogen and a carbon atom of the heteroatom-containing chain to form a ring, and wherein the ring is optionally fused to an Ar' group, or

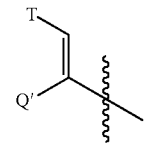

wherein Q' is hydrogen, (C1-C6)-straight or branched alkyl or (C2-C6)-straight or branched alkenyl or alkynyl;

wherein T' is Ar or substituted 5-7 membered cycloalkyl with substituents at positions 3 and 4 that are independently selected from the group consisting of oxo, hydrogen, hydroxyl, O—(C1-C4)-alkyl, and O—(C2-C4)-alkenyl;

wherein Ar' is a carboxcyclic aromatic group selected from the group consisting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;

wherein Ar' may contain one to three substituents that are independently selected from the group consisting of hydrogen, halogen, hydroxyl, hydroxymethyl, nitro, trifluoromethyl, trifluoromethoxy, (C1-C6)-straight or branched alkyl, (C2-C6)-straight or branched alkenyl, O—[(C1-C4)-straight or branched alkyl], O—[(C2-C4)-straight or branched alkenyl], O-benzyl, O-phenyl, 1,2-methylenedioxy, amino, carboxyl, N—[(C1-C5)-straight or branched alkyl or (C2-C5)-straight or branched alkenyl)carboxamides, N,N-di[(C1-C5)-straight or branched alkyl or (C2-C5)-straight or branched alkenyl]carboxamides, N-morpholinocarboxamide, N-benzylcarboxamide, N-thiomorpholinocarboxamide, N-picolinoylcarboxamide, O—X, $CH_2$—$(CH_2)_q$—X, O—$(CH_2)_q$—X, $(CH_2)_q$—O—X, and CH═CH—X;

wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl: and α is 0-2;

wherein G is U';

wherein M is either oxygen or CH—U'; provided that if G is hydrogen, then M is CH—U' or if M is oxygen, then G is U';

wherein U' is hydrogen, O—[(C1-C4)-straight or branched alkyl]or O—[(C2-C4)-straight or branched alkenyl], (C1-C6)-straight or branched alkyl or (C2-C6)-straight or branched alkenyl, (C5-C7)-cycloalkyl or (C5-C7)-cycloalkenyl substituted with (C1-C4)- straight or branched alkyl or (C2-C4)-straight or branched alkenyl, [(C1-C4)-alkyl or (C2-C4)-alkenyl]-Y or Y;

wherein Y is selected from the group consisting of phenyl, 1-naphthyl, 2-naphthyl, indenyl, azulenyl, fluorenyl, anthracenyl, 2-pyrrolinyl, 3-pyrrolinyl, pyrolidinyl, 1,3-dioxolyl, 2-imidazolinyl, imidazolidinyl, 2H-pyranyl, 4H-pyranyl, piperidyl, 1,4-dioxanyl, morpholinyl, 1,4-dithianyl, thiomorpholinyl, piperazinyl, quinuclidinyl, and heterocyclic aromatic groups as defined for Ar' above;

wherein Y may contain one to three substituents that are independently selected from the group consisting of hydrogen, halogen, hydroxyl, hydroxymethyl, nitro, trifluoromethyl, trifluoromethoxy, (C1-C6)-straight or branched alkyl, (C2-C6)-straight or branched alkenyl, O—[(C1-C4)-straight or branched alkyl], O—[(C2-C4)-straight or branched alkenyl], O-benzyl, O-phenyl, 1,2-methylenedioxy, amino, and carboxyl;

wherein J' is hydrogen, (C1-C2) alkyl or benzyl; wherein K is (C1-C4)-straight or branched alkyl, benzyl or cyclohexylmethyl, or wherein J' and K may be taken together to form a 5-7 membered heterocyclic ring that may contain a heteroatom selected from the group consisting of O, S, SO and SO$_2$;

wherein m is 0-3; and wherein the stereochemistry at position 1 is R or S and the stereochemistry at position 2 is R or S.

(3) Compounds represented by the formula III (see Armistead et al., *Acta Cryst.* D51:522-528, 1995, including a discussion of selection of R and of the synthesis of these compounds, the disclosure of which is incorporated herein by reference):

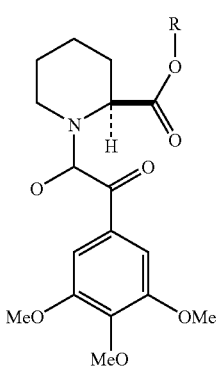

(III)

(4) Compounds represented by the formula IV (see WO 92/21313, including a discussion of the synthesis of these compounds, the disclosure of which is incorporated herein by reference):

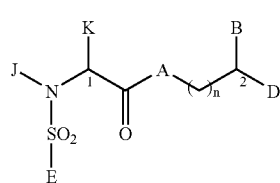

(IV)

wherein A is CH$_2$, oxygen, NH or N—(C1-C4 alkyl);

wherein B and D are independently Ar, hydrogen, (C1-C6)-straight or branched alkyl, (C1-C6)-straight or branched alkenyl, (C1-C6)-straight or branched alkyl or alkenyl that is substituted with a (C5-C7)-cycloalkyl, (C1-C6)-straight or branched alkyl or alkenyl that is substituted with a (C5-C7)-cycloalkenyl, or Ar substituted (C1-C6)-straight or branched alkyl or alkenyl, wherein, in each case, one or two of the CH$_2$ groups of the alkyl or alkenyl chains may contain 1-2 heteroatoms selected from the group consisting of oxygen, sulfur, SO and SO$_2$ in chemically reasonable substitution patterns, or

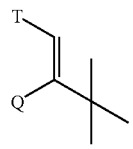

provided that both B and D are not hydrogen;

wherein Q is hydrogen, (C1-C6)-straight or branched alkyl or (C1-C6)-straight or branched alkenyl;

wherein T is Ar or substituted 5-7 membered cycloalkyl with substituents at positions 3 and 4 that are independently selected from the group consisting of hydrogen, hydroxyl, O—(C1-C4)-alkyl, O—(C1-C4)-alkenyl and carbonyl;

wherein Ar is selected from the group consisting of phenyl, 1-naphthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 that may contain in either or both rings a total of 1-4 heteroatoms independently selected from O, N and S; wherein Ar may contain one to three substituents that are independently selected from the group consisting of hydrogen, halo, hydroxyl, nitro, trifluoromethyl, trifluoromethoxy, (C1-C6)-straight or branched alkyl, (C2-C6)-straight or branched alkenyl, O—(C1-C4)-straight or branched alkyl, O—(C2-C4)-straight or branched alkenyl, O-benzyl, O-phenyl, 1,2-methylenedioxy, amino, carboxyl and phenyl;

wherein E is (C1-C6)-straight or branched alkyl, (C1-C6)-straight or branched alkenyl, (C5-C7)-cycloalkyl, (C5-C7)-cycloalkenyl substituted with (C1-C4)-straight or branched alkyl or (C1-C4)-straight or branched alkenyl, [(C2-C4)alkyl or (C2-C4)-alkenyl)]-Ar or Ar (Ar as described above);

wherein J is hydrogen or C1 or C2 alkyl or benzyl; K is (C1-C4)-straight or branched alkyl, benzyl or cyclohexylmethyl; or wherein J and K may be taken together to form a 5-7 membered heterocyclic ring that may contain an oxygen, sulfur, SO or SO$_2$ substituent therein; and;

wherein n is 0-3; and wherein the stereochemistry at position 1 is R or S and the stereochemistry at position 2 being R or S.

(5) Compounds represented by the formula V (see WO 92/04370, including a discussion of the synthesis of these compounds, the disclosure of which is incorporated herein by reference):

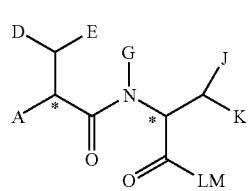

(V)

wherein A is NH, O, S, or CH;

wherein if A is NH, O, or S, B is PCO— or POCO—, where P is a C1-C6 straight or branched alkyl or alkenyl group, a C5-C6 cycloalkyl or cycloalkenyl, or a methyl substituted with a C5-C6 cycloalkyl, C5-C6 cycloalkenyl, phenyl, 1-naphthyl, 2-naphthyl, 9-fluorenyl, or 1-adamantyl;

wherein if A is CH, then B is connected via a trans double bond and is a C2-C4 straight or branched alkyl or alkenyl group, or is a methyl or ethyl substituted with either a C5-C6 cyclic alkyl group or Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1-C4 straight or branched alkyl or alkenyl, O—(C1-C4) straight or branched alkyl or alkenyl, and Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1-C4 straight or branched alkyl or alkenyl, O—(C1-C4) straight or branched alkyl or alkenyl; wherein no more than two Ar groups may be linked together;

wherein D is hydrogen, C1-C4 straight or branched alkyl or alkenyl, hydroxy, tert-butyloxy, benzyloxy, 4-benzyloxyphenyl, cyclohexyl, —$(CH_2)_n$—$CO_2$-Q, where n=0 or 1 and Q is methyl, ethyl, i-propyl, t-butyl, benzyl, 1-naphthyl, 2-naphthyl, or cyclohexyl; or Ar, where Ar is selected from the group consisting of 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1-C4 straight or branched alkyl or alkenyl, O—(C1-C4) straight or branched alkyl or alkenyl, and Ar, where Ar is selected from the group consisting of 1-naphthyl, 2-naphthyl, 2-furyl, 3-furyl, 2-thienyl, phenyl and phenyl having one to three substituents that are independently selected from the group consisting of:hydroxyl, halo, nitro, $CF_3$, C1-C4 straight or branched alkyl or alkenyl, O—(C1-C4) straight or branched alkyl or alkenyl;

wherein no more than two Ar groups may be linked together;

wherein E and K are independently hydrogen or methyl;

wherein G is either methyl or ethyl; J is hydrogen, C1-C6 straight or branched alkyl or alkenyl, C6-C6 cycloalkyl or cycloalkenyl, sulfhydryl, hydroxy, phenyl, 3-indolyl, or benzyl; wherein G and J may be connected by a bond to form a cycle of 5 or 6 members;

wherein L is O or an α-amino acid residue attached via the α-nitrogen, and selected from the group consisting of:alanine, 2-aminobutyric acid, valine, norvaline, leucine, norleucine, isoleucine, phenylalanine, cyclohexylalanine, tryptophan, 1-naphthylalanine, 2-naphthylalanine, threonine (side chain benzyl or tert-butyl ether), methionine, or serine (side chain benzyl or tert-butyl ether);

wherein if L is O, then M is C1-C6 straight or branched alkyl or alkenyl, or —$(CH_2)_n$—Ar, where n=1-6 and Ar is selected from the group consisting of: 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1-C4 straight or branched alkyl or alkenyl, O—(C1-C4) straight or branched alkyl or alkenyl, and Ar, wherein Ar is selected from the group consisting of: 1-naphthyl, 2-naphthyl, 2-furyl, 3-furyl, 2-thienyl, phenyl and phenyl having one to three substituents that are independently selected from the group consisting of: hydroxyl, halo, nitro, $CF_3$, C1-C4 straight or branched alkyl or alkenyl, O—(C1-C4) straight or branched alkyl or alkenyl; wherein no more than two Ar groups may be linked together;

wherein if L is an amino acid, then M is O—(C1-C4) straight or branched alkyl, O-benzyl, NH-Phenyl, or NH-4-nitrophenyl and is attached to the amino acid carbonyl;

the stereochemistry at all positions being R or S, and preferably the stereochemistry is S at L if L is an α-amino acid, and at those positions marked with asterisks; however, when J is sulfhydryl, the preferred stereochemistry of the asterisked position immediately adjacent to the nitrogen is R.

(6) Compounds represented by the formula VI (see WO 96/40633, including a discussion of the synthesis of these compounds, the disclosure of which is incorporated herein by reference):

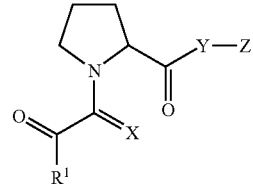

(VI)

wherein, R1 is selected from the group consisting of a C1-C9 straight or branched chain alkyl or alkenyl group optionally substituted with C3-C8 cycloalkyl, C3 or C5 cycloalkyl, C5-C7 cycloalkenyl, or Ar1, where said alkyl, alkenyl, cycloalkyl or cycloalkenyl groups may be optionally substituted with C1-C4 alkyl, C1-C4 alkenyl, or hydroxy, where Ar1 is selected from the group consisting of 1-naphthyl, 2-naphthyl, 2-indolyl, 3-indolyl, 2-furyl, 3-furyl, 2-thiazolyl, 2-thienyl, 3-thienyl, 2-, 3-, 4-pyridyl, and phenyl, having one to three substituents that are independently selected from the group consisting of hydrogen, halo, hydroxyl, nitro, trifluoromethyl, C1-C6 straight or branched alkyl or alkenyl, C1-C4 alkoxy or C1-C4 alkenyloxy, phenoxy, benzyloxy, and amino;

wherein X is selected from the group consisting of oxygen, sulfur, methylene ($CH_2$), or $H_2$;

wherein Y is selected from the group consisting of oxygen or $NR_2$, where $R_2$ is hydrogen or C1-C6 alkyl; and wherein Z is selected from the group consisting of C2-C6 straight or branched chain alkyl or alkenyl, wherein the alkyl chain is substituted in one or more positions with $Ar_1$ as defined above, C3-C8 cycloalkyl, cycloalkyl connected by a C1-C6 straight or unbranched alkyl or alkenyl chain and $Ar_2$, where $Ar_2$ is selected from the group consisting of 2-indolyl, 3-indolyl, 2-furyl, 3-furyl, 2-thiazolyl, 2-thienyl, 3-thienyl, 2-, 3-, or 4-pyridyl, and phenyl, having one to three substituents that are independently selected from the group consisting of hydrogen, halo, hydroxyl, nitro, trifluoromethyl, C1-C6 straight or branched alkyl or alkenyl, C1-C4 alkoxy or C1-C4 alkenyloxy, phenoxy, benzyloxy, and amino;

wherein Z may also be the fragment:

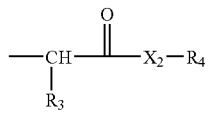

where
- R$_3$ is selected from the group consisting of straight or branched alkyl C1-C8 optionally substituted with C3-C8 cycloalkyl, or Ar$_1$ as defined above, and unsubstituted Ar$_1$;
- X$_2$ is O or NR$_5$, where R$_5$ is selected from the group consisting of hydrogen, C1-C6 straight or branched alkyl and alkenyl;
- R$_4$ is selected from the group consisting of phenyl, benzyl, C1-C5 straight or branched alkyl or alkenyl, and C1-C5 straight or branched alkyl or alkenyl substituted with phenyl;
- wherein the stereochemistry at position 1 is R or S.

Also encompassed are pharmaceutically acceptable derivatives of the FK506 analogs, including, but not limited to, any pharmaceutically acceptable salt, ester, salt of an ester, or any other derivative which, upon administration to a patient, is capable of providing directly or indirectly a non-binding FK506 analog or a metabolite or residue thereof that has the desired neurotrophic activity. Included within the scope of the invention are enantiomers, the racemic form, and diastereoisomeric mixtures. Enantiomers and diastereoisomers can be separated by conventional methods.

A "non-binding FK506 analog" is defined as an FK506 analog that does not bind to FKBP-12. Preferably, such FK506 analogs bind FKBP-12 with an apparent K$_d$ of greater than 10 µM as measured using well-known assays, and preferably greater than 30 µM, and more preferably greater than 100 µM. Values for the apparent K$_d$ can be determined, for example, by a competitive LH-20 binding assay performed as described, for example, in:Harding et al., Nature 341:758-760, 1989 (using 32-[1-$^{14}$C]-benzoyl FK506 as a reporting ligand; Siekierka et al., Nature 341: 755-757, 1989, using [$^3$H]dihydro-FK506 as a reporting ligand); and U.S. Pat. No. 5,654,332.

Alternatively, a "non-binding FK506 analog" is defined as an FK506 analog that does not significantly inhibit FKBP-12 rotamase activity when administered to a patient at dosage levels of about 0.01 to about 100 mg/kg body weight/day. Assays for inhibition of FKBP-12 rotamase activity are described in Harding et al. (Nature 341:758-760, 1989), Siekierka et al., Nature 341:755-757, 1989, and U.S. Pat. No. 5,654,332, for example. Chymotrypsin is able to cleave p-nitroanilide from the trans form of the artificial substrate N-succinyl-Ala-Ala-Pro-Phe-p-nitroanilide, but not from the cis form. The assays of Harding et al. and Siekierka et al. employ a reaction mixture that includes the cis form of N-succinyl-Ala-Ala-Pro-Phe-p-nitroanilide, FKBP-12, a test compound, and chymotrypsin, and spectrophotometrically measure the release of p-nitroanilide as a result of isomerization of the substrate.

Formulae I-VI above represent compounds that have a wide range of binding affinities for FKBP-12. Non-binding FK506 analogs can be readily identified by well-known assays for FKBP-12 binding or rotamase activity. Non-binding compounds can then be readily assessed for activity in promoting regeneration of nerve cells by the in vitro and in vivo assays discussed in the Examples below. The non-binding FK506 analogs are non-immunosuppressive, as can be demonstrated by well-known assays, e.g., as discussed in U.S. Pat. No. 5,516,797, WO 92/21313, WO 92/19593, and WO 92/04370.

FK506 analogs can be used in the form of salts preferably derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, e.g., with such agents as lower alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

As would be apparent to the person of ordinary skill in the art, the nonbinding FK506 analogs can be modified by appending appropriate functionalities by well-known methods to enhance selected biological properties, including increasing penetration of the analogs into a given cellular compartment (e.g., blood, lymphatic system, central nervous system, etc.), increase oral availability, increase solubility to permit administration by injection, alter metabolism, and alter rate of excretion, for example.

Preferably, the FK506 analogs have a molecular weight below about 750 atomic mass units (a.m.u.) (as the parent compound, although the salts of such compounds can have higher molecular weights).

An "effective amount" of a composition according to the invention is an amount sufficient to achieve a statistically significant promotion of nerve cell growth or regeneration compared to a control. Nerve cell growth or regeneration can be readily assessed using an in vitro assay, e.g., the assay described in the Examples below. Alternatively, nerve cell growth or regeneration can be determined in an in vivo assay or by direct or indirect signs of nerve cell growth and regeneration in a patient. Preferably, the increase in nerve cell growth or regeneration is at least 10%, preferably at least 30%, and most preferably 50% or more compared to a control. Preferred dosage levels are between about 0.1 to about 400 mg/kg per day of the FK506 analog.

Therapeutic and Prophylactic Uses

FK506 analogs can be periodically administered to a mammal, including a human patient in need of such treatment, to promote neuronal regeneration and functional recovery and to stimulate neurite outgrowth and thereby to treat various neuropathological states, including damage to peripheral nerves and the central nervous system caused by physical injury (e.g., spinal cord injury and trauma, sciatic crush, and facial nerve crush), disease (e.g., diabetic neuropathy), cancer chemotherapy (e.g., by vinca alkaloids and doxorubicin), brain damage associated with stroke and ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, dapsone, ticks, porphyria, Gullain-Barré syndrome, Alzheimer's disease, Parkinson's disease, and Huntington's chorea.

In addition, pharmaceutical compositions according to the present invention display a wide range of other therapeutic or prophylactic properties, including, treatment of stroke (see, e.g., Sharkey and Butcher, *Nature* 371:336-339, 1994, Vagita et al., *Life Sciences* 59:1643-1650, 1996; Tokime et al., *Neurosci. Lett.* 206:81-84, 1996; Drake et al., *Acta. Physiol. Scand* 158:155-159, 1996; and Kuroda et al., *Neurosci. Res. Comm.* 19:83-90,1996), AIDS dementia (see, e.g., Dawson and Dawson, *Adv. Neuroimmunol.* 4:167-173, 1994; and Sekigawa et al., *J. Clin. Immunol.* 15:312-317, 1995); hair growth (Yamamoto et al., *J. Investig. Dermatol.* 102:160-164, 1994; Jiang et al., *J. Investig. Dermatol.* 104:523-525, 1995); and connective tissue disorders (see e.g., Steinmann et al., *J. Biol. Chem.* 266:1299-1303, 1991), and as a male contraceptive (see e.g., Hisatomi et al., *Toxicology* 109:75-83, 1996).

Pharmaceutical Formulations

Pharmaceutical formulations according to the present invention encompass formulations comprising (1) an amount (for example, a unit dosage) of a non-binding FK506 analog together with (2) one or more well-known non-toxic pharmaceutically acceptable excipients, including carriers, diluents, and/or adjuvants, and optionally (3) one or more biologically active ingredients. Standard pharmaceutical formulation techniques are used, such as those disclosed in *Remington's Pharmaceutical Sciences*, Mack Publishing Co., Easton, Pa. (latest edition).

A pharmaceutical formulation according to the invention can include a single non-binding FK506 analog or combination of a non-binding FK506 analog with one or biologically active ingredients, including, but not limited to: (1) one or more non-binding FK506 analogs; (2) one or more FKBP-12-binding FK506 analogs; (3) one or more other neurotrophic agents, including, for example, NGF, IGF-1, aFGF, bFGF, PDGF, BDNF, CNTF, GDNF, NT-3, and NT 4/5; and so on.

It is preferred that the pharmaceutical formulation includes an amount of a neurotrophic agent(s), preferably NGF, such that the patient receives a dosage of between about 0.01 to 100 μg/kg body weight/day of the neurotrophic agent, or that the neurotrophic agent be administered separately, e.g., in separate single or multiple dosage forms, preferably concurrently, consecutively, or within less than about five hours of each other.

The compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Such pharmaceutical compositions can be administered systemically or locally in any manner appropriate to the treatment of a given condition, including orally, parenterally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions preferably readily penetrate the blood-brain barrier when peripherally administered or are administered intraventricularly.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat, for example.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. The tablets can be coated according to methods well known in normal pharmaceutical practice. Oral liquid preparations can be in the form of, for example, aqueous or oily suspensions, solutions, emulsions, syrups or elixirs, or can be presented as a dry product for reconstitution with water or other suitable vehicle before use. Such liquid preparations can contain conventional additives such as suspending agents, e.g., sorbitol, syrup, methyl cellulose, glucose syrup, gelatin, hydrogenated edible fats, emulsifying agents, e.g., lecithin, sorbitan monooleate, or acacia; non-aqueous vehicles (including edible oils), e.g., almond oil, fractionated coconut oil, oily esters such as glycerine, propylene glycol, or ethyl alcohol; preservatives such as methyl or propyl p-hydroxybenzoate or sorbic acid, and, if desired, conventional flavoring or coloring agents.

Pharmaceutical compositions according to the present invention can also be administered parenterally in a sterile aqueous or oleaginous medium. The composition can be dissolved or suspended in a non-toxic parenterally-acceptable diluent or solvent, e.g., as a solution in 1,3-butanediol. Adjuvants such as local anesthetics, preservatives, and buffering agents can also be dissolved in the vehicle. Commonly used vehicles and solvents include water, physiological saline, Hank's solution, Ringer's solution, and sterile, fixed oils, including synthetic mono- or di-glycerides, etc. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as Ph. Helv or a similar alcohol.

For topical application, the drug may be made up into a solution, suspension, cream, lotion, ointment in a suitable aqueous or non-aqueous vehicle. Additives may also be included, e.g., buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels on the order of about 0.1 to about 400 mg/kg per day of the active ingredient are useful in the treatment of the conditions listed above.

The invention will be better understood by reference to the following examples, which are intended to merely illustrate the best mode now known for practicing the invention. The scope of the invention is not to be considered limited thereto, however.

EXAMPLE 1

A Non-Immunosuppressant FKBP-12 Ligand Increases Nerve Regeneration

Materials and Methods

Cell cultures. SH-SY5Y human neuroblastoma cells were maintained in DMEM medium (GIBCO) supplemented with 10% fetal calf serum (SIGMA), 50 IU>mL penicillin, and 50 mg/ml streptomycin (GIBCO) at 37° C. in 7% $CO^2$. Cells were plated in six-well plates at $1\times10^6$ cells/well and treated with 0.4 mM aphidicolin (SIGMA). At five days, cells were washed, treated with nerve growth factor (NGF) (Boehringer Mannheim, Indianapolis, Ind.) at 10 ng/mL (to induce process outgrowth) in the presence or absence of V-10,367 (1, 10, or 100 nM) (Armistead et al., *Acta Cryst.*, D51:522-528, 1995; FIG. 1). Media was changed at 96 hours and replaced with fresh media with or without the compounds (NGF and V-10,367) for an additional 72 hours (total time, 168 hours). All experiments were run in duplicate wells and repeated at least twice for reproducibility.

Light morphometry of neurite lengths. For analysis of process length, cells 20 fields per well) were randomly photographed at 72 and 168 hours. Neurite lengths were measured on photographic prints using a Houston Instrument HI-PAD digitizing tablet connected to an IBM XT computer with appropriate software (Bioquant IV, R&M Biometrics, Nashville, Tenn.); only those processes greater than two times the cell body length were measured. Data from identically treated wells were not different and were therefore combined. Mean values and histograms were constructed from these data. Histograms were compared using a Mann-Whitney U test, which makes no assumptions about the shape of the distribution.

Animals and surgical procedure. Ten six-week-old Sprague-Dawley rats were anesthetized with 2% halothane, the right sciatic nerve exposed, and the nerve crushed twice (for a total of 30 sec using a No. 7 Dumont jeweler's forceps) at the level of the hip. The crush site was marked by tying a sterile 9-0 suture through the perineurial sheath.

Preparation and administration of V-10,367. V-10,367-HCl (molecular weight, 639.18) was dissolved in vehicle comprising 40% propylene glycol:10% ethanol:50% water. Fresh solutions were prepared at the time of each injection. Three rats received subcutaneous injections (200 mg/kg) every 12 hours (beginning immediately after the nerve crush; totaling 400 mg/kg/day) in the back of the neck using a 25 g needle. Control animals (n=3) received injections every 12 hours of vehicle only. An additional control group (n=3) received daily injections of saline. Animals were weighed daily and the weights plotted over the 18-day period of the study.

Two separate additional studies were performed. In the first study, three axotomized rats received a single daily subcutaneous injection (200 mg/kg) as above. In the second study, V-10,367 was delivered as to axotomized rats as a continuous infusion. Osmotic pumps (Alza, Palo Alto, Calif.) model 2ML2 filled with V-10,367-HCl (200 mg/ml) or vehicle (two per group) were implanted under the skin on the left side of the animal. This lot of 2ML2 pumps (lot#043503) had a mean pumping rate of 4.84 mL/hour, a mean fill volume of 2229 mL, and were capable of delivering fluid for a total of 18.3 days.

Behavioral assessment. Functional recovery was assessed in FK506-treated animals used for morphological study only. Animals were examined blindly by two investigators daily until the day of perfusion (18 days). The number of days following nerve crush until the animal demonstrated onset of an ability to right its foot and move its toes (termed "onset"), and the number of days until the animal demonstrated an ability to walk on its hind feet and toes (termed "walking") were recorded for each animal. To obtain records during walking, the hind feet were marked with tempera paint and the animals allowed to freely walk across a sheet of paper between 14-18 days. Toe spread during walking was defined as the distance between the first and fifth digits, measured to the nearest 0.5 mm; three foot prints were analyzed from each animal. This analysis represents a reliable and reproducible index of functional recovery which, unlike the sciatic nerve function index, is not influenced by how fast the animal walks (Walker et al., *Restor. Neurol. Neurosci.* 6:189-193, 1994).

Tissue fixation and preparation. At 18 days after nerve crush, the rats were deeply anesthetized with 4% halothane, heparinized, and perfused with 4% paraformaldehyde in 0.1 M sodium phosphate buffer (pH 7.4) and fixed at 4° C. for 24 hours. Tissues were sampled from the sciatic nerve at known (0.5 mm) distances from the crush site (see Gold et al., *Restor. Neurol. Neurosci.* 6:287-296, 1994). In the present study, only the data from the branch of the posterior tibial nerve supplying the soleus muscle are reported. Tissues were placed in 0.1 M sodium phosphate buffer (pH 7.4), postfixed with 2% osmium tetroxide (in 0.1 M phosphate buffer) for 2.5 hours, dehydrated in ethanol, and embedded in plastic. Semithin sections (0.5 mm) were stained with toluidine blue; thin sections were stained with uranyl acetate and lead citrate, mounted on film-supported 75 mesh grids, and examined in a JOEL 100x electron microscope.

Electron microscopic analysis of axons. Analysis of axonal calibers was performed in soleus nerve. The entire nerve was photographed and printed at a final magnification of 10,000x. Axonal areas of both myelinated and unmyelinated fibers were determined by tracing the axolemma using a Houston Instrument HI-PAD digitizing tablet connected to an IBM XT computer with appropriate software (Bioquant IV, R&M biometrics, Nashville, Tenn.). Cumulative histograms were constructed from these data and mean values and standard errors were calculated. For each group (i.e., 400 and 200 mg/kg/day V-10,367-treated and vehicle-treated), mean values and standard areas were calculated for the whole population of axons. Mean values for axonal areas were compared using a one-way analysis of variance (ANOVA) followed Fischer's test of least significant differences for comparison of individual values (STATVIEW, Abacus Concepts, Inc., Berkeley, Calif.). Since axonal areas did not demonstrate a normal distribution, the largest 30% of axons was selected from each animal (i.e., each nerve), and these values were used to construct histograms of the top 30% of axons. Histograms were compared using the Mann-Whitney U test. These tests confirmed the ANOVA results, and these latter values are discussed herein.

Results

Figure 2A:
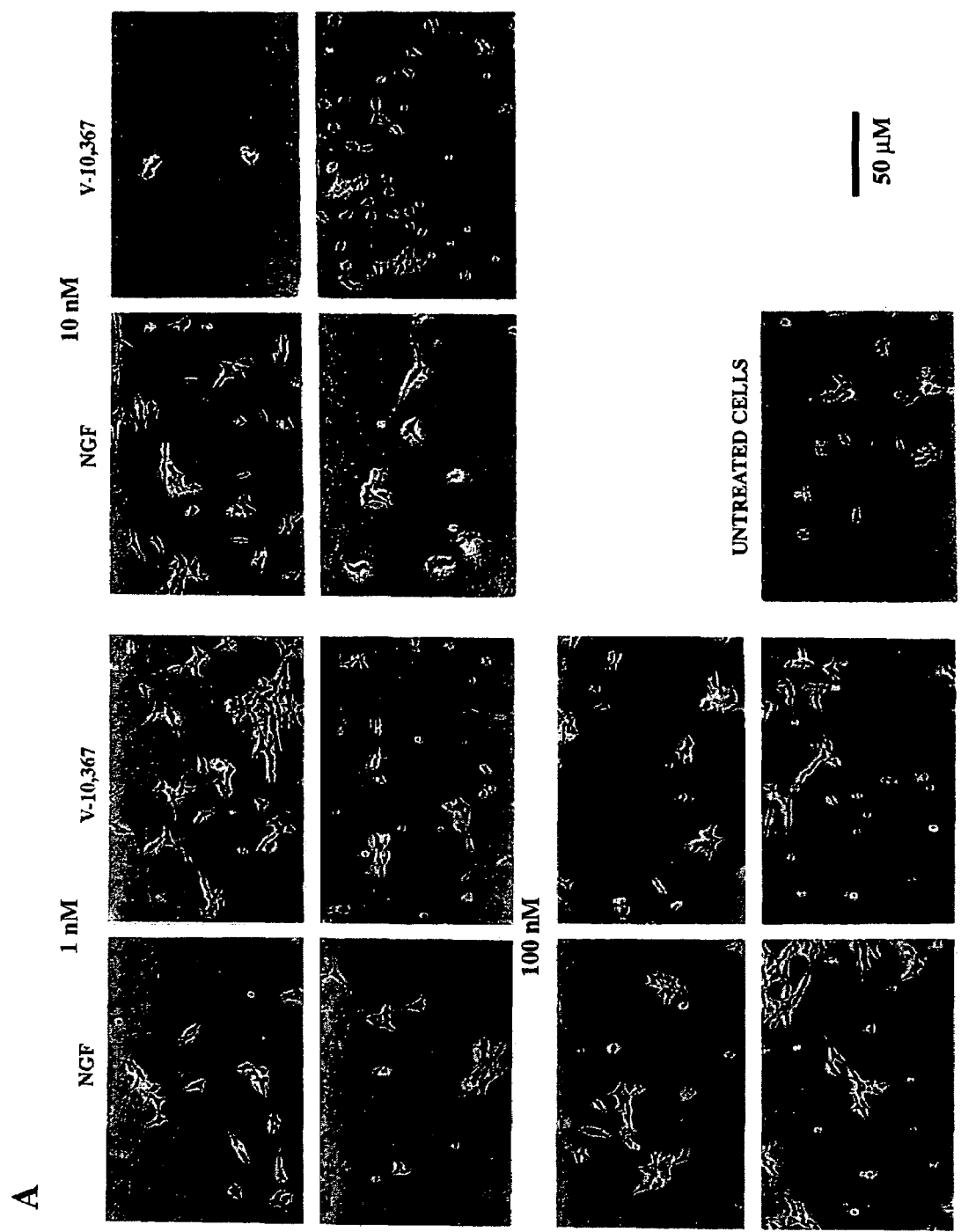
FIG. 2A shows SH-SY5Y neuroblastoma cells treated with NGF (10 ng/mL) alone or in the presence of V-10,367 (1, 10, or 100 nM). Representative micrographs at each concentration are shown at 96 hours (top row) and 168 hours (bottom row); the micrograph at the far bottom right shows untreated cells (at 168 hours). At each concentration, the micrograph on the left shows the effect of NGF only, whereas the micrograph of the right shows the effect of NGF plus V-10,367. Magnification:145×.
Figure 2B:
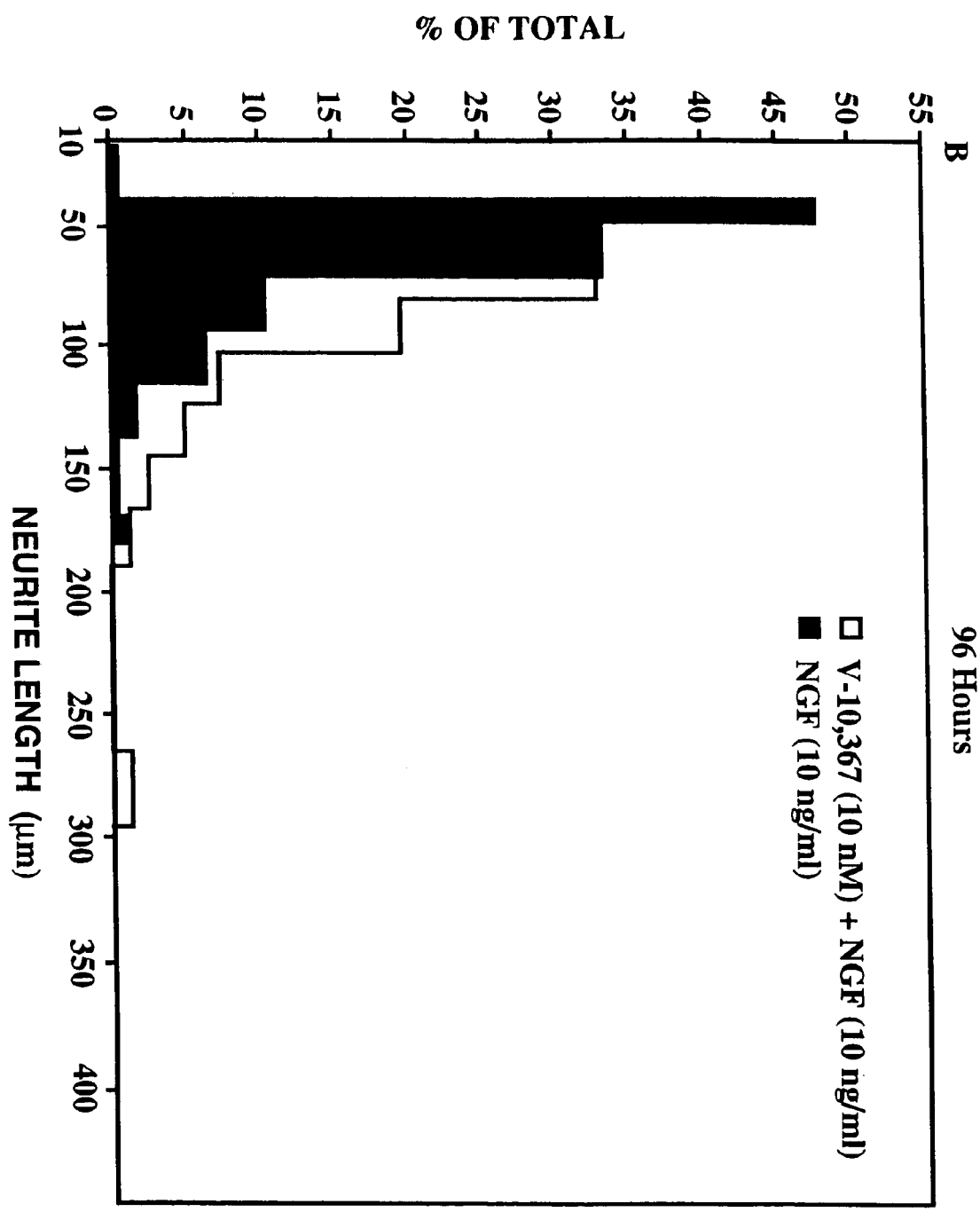
FIG. 2B is a histogram showing the effect of 10 nM V-10,367 on the distribution of SH-SY5Y neurite lengths at 96 hours. The histograms from the V-10,367-treated cells (open histograms) are shifted to the right (indicating longer processes) compared to NGF only (closed histograms). There is a greater skewing to the right in the histograms from the V-10,367-treated cells due to the presence of more neurites with very long processes. Similar results were obtained in two replicate experiments.
Figure 2C:
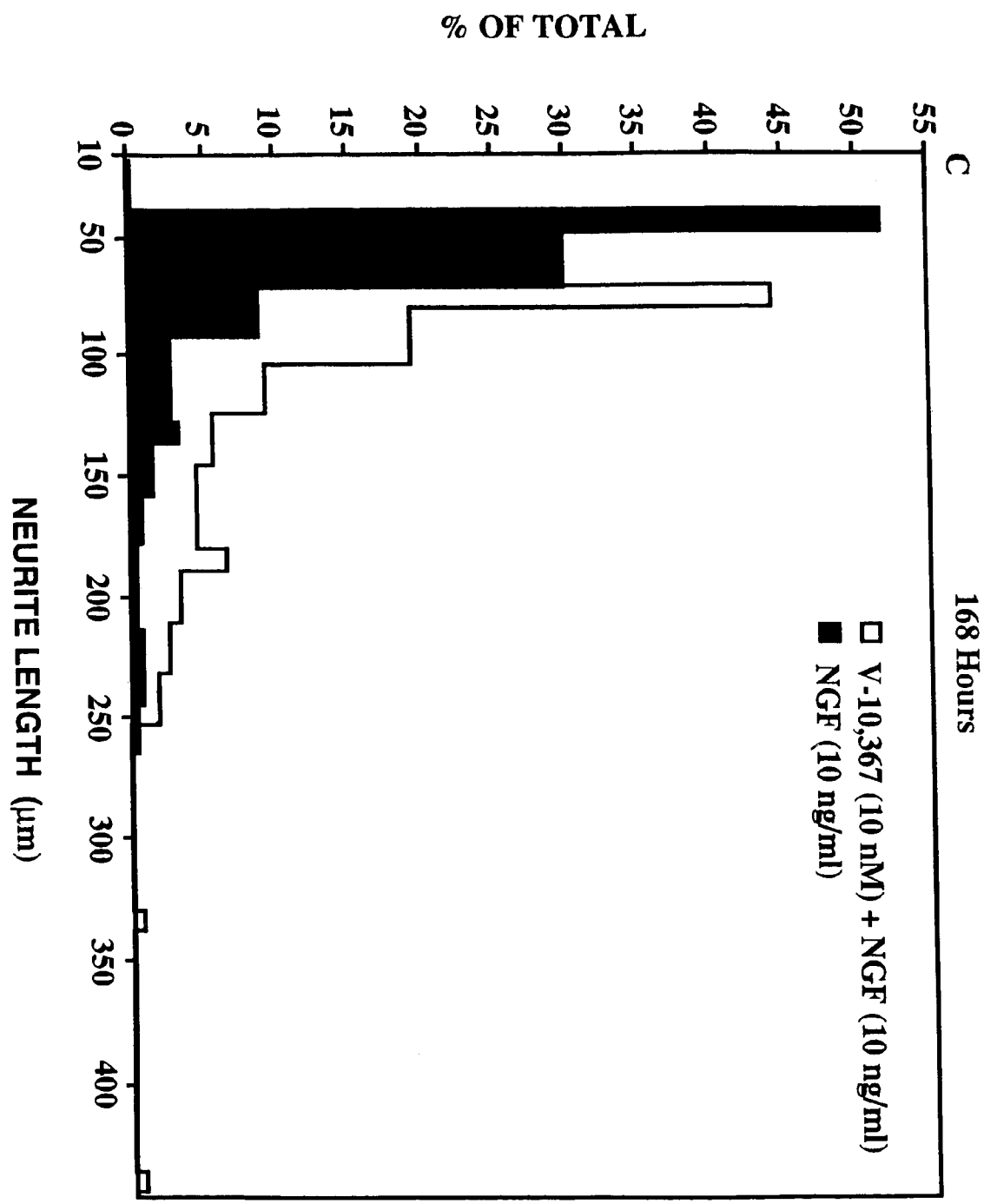
FIG. 2C is a histogram (similar to FIG. 2B) showing the effect of 10 nM V-10,367 on the distribution of SH-SY5Y neurite lengths at 168 hours.

Neurite outgrowth. We first tested whether V-10,367 is able to increase neurite growth in vitro. SH-SY5Y neuroblastoma cells developed long axonal-like processes upon exposure to NGF (10 ng/mL), which were dramatically increased in length by V-10,367 at both 1 nM and 10 nM concentrations (FIG. 2). Representative micrographs at 96 and 168 hours for all three concentrations are shown in FIG. 2A. Measurement of the lengths of neurite processes demonstrated that the ability of V-10,367 to increase the length of neurite processes was concentration-dependent between 1 and 10 nM and time-dependent between 96 and 168 hours (Table 1). The distribution of lengths of neurite processes was not a normal distribution, which necessitated direct comparison of histograms using non-parametric statistics. Histograms constructed from these data (shown for 10 nM only) demonstrated a significant ($p<0.05$; Mann-Whitney U-test) shift to longer neurite processes at 96 hours (FIG. 2B) and 168 hours (FIG. 2C).*compared* to NGF (10 ng/mL) alone. There was a greater skewing to the right in histograms from V-10,367-treated cells due to the presence of more neurites with very long processes. Neurite lengths showed a concentration-dependent increase over time, the maximal effect being observed at the 10 nM concentration. At all concentrations, V-10,367 increased neurite outgrowth compared to NGF alone, but process lengths were not as long at 100 nM V-10,367 as at 10 nM. No change in the number of processes per cell or branching of cell processes was observed (FIG. 2A). Similar results were obtained in two replicate experiments.

Pharmacokinetics of V-10,367. To determine the appropriate daily dose of V-10,367 for administration to rats, single-dose pharmacokinetics of V-10,367 were evaluated in the rat following intravenous and subcutaneous dosing. Following a single intravenous dose of 17.7 mg/kg of V-10,367 in the Sprague-Dawley rat, V-10,367 was found to have an average blood clearance of 5.04 L/hr/kg and an elimination half-life of about 1.3 hours. The volume of distribution at steady state was determined to be 2.76 L/kg, suggesting extensive tissue distribution. A subcutaneous injection of 174 mg/kg showed an average $C_{max}$ of 171 ng/mL (285 nM). The apparent half-life of V-10,367 was prolonged following subcutaneous administration, and trough concentrations at 8 hours post-dose ranged between 27-252 ng/mL (45-420 nM). Since these concentrations were sufficiently above the 10 nM concentration needed to cause neurite extension in vitro, a subcutaneous dose of 200 mg/kg twice daily was selected for subsequent experiments.

Figure 3:
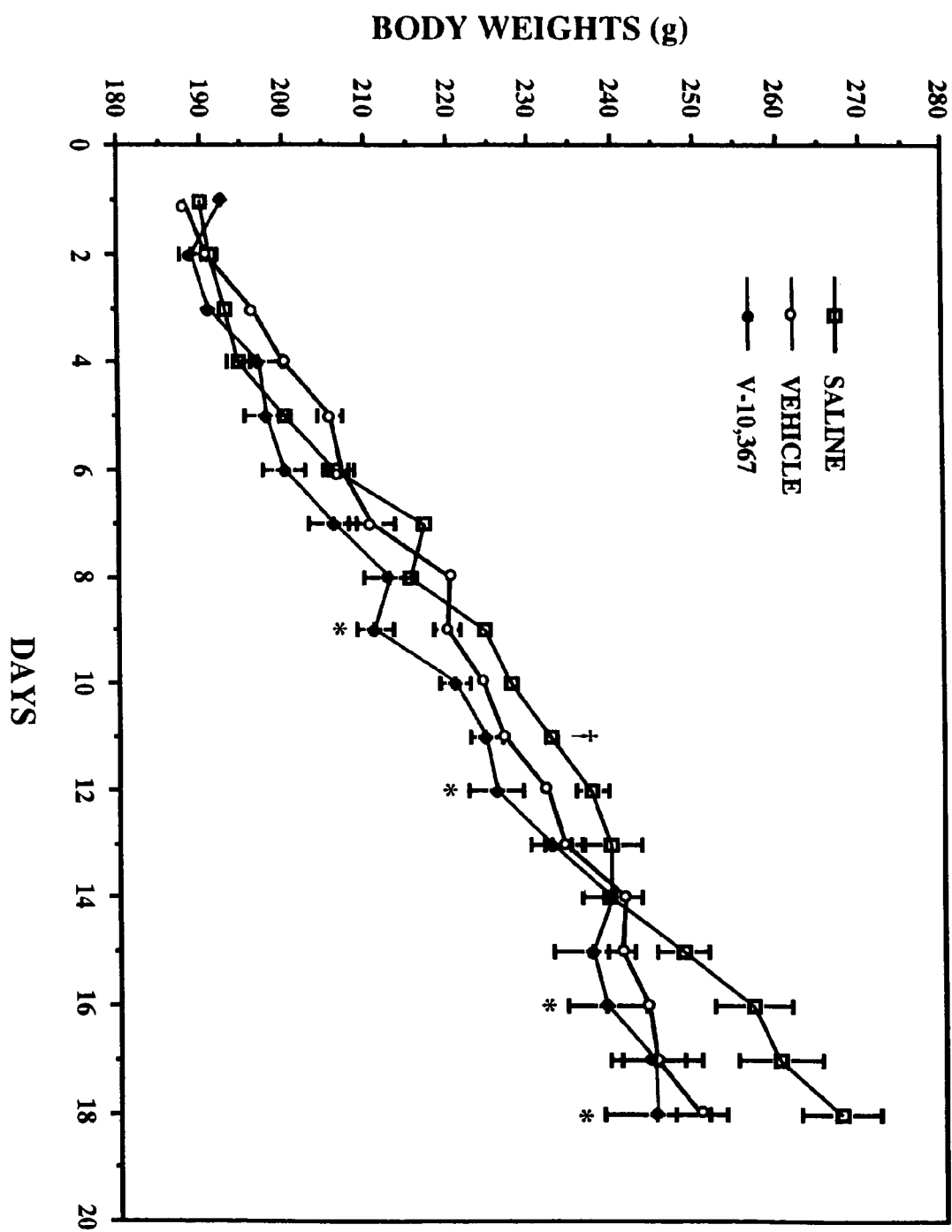
FIG. 3 is a plot of mean body weights during an 18-day treatment period from saline-treated (open squares), vehicle-treated (open circles), and V-10,367-treated (closed circles) axotomized rats. Day 0 corresponds to the time of axotomy. *p<0,05, compared to saline-treated animals (by ANOVA and Fischer's post hoc test);$^{H}$p<0.05, compared to vehicle-treated and V-10,367-treated animals (by ANOVA and Fischer's post hoc test).

Nerve regeneration. The ability of V-10,367 to accelerate nerve regeneration was examined in the rat sciatic nerve. Following a unilateral (right side) sciatic nerve crush, male rats were given subcutaneous injections of V-10,367 (n=3) or vehicle (n=3) every 12 hours totaling 400 mg/kg/day in the drug-treated group. The compound appeared to be well tolerated by the animals following repeated subcutaneous injections for up to 18 days. Both the V-10,367-treated and vehicle-treated animals continued to gain weight, albeit at a similar slightly reduced rate compared to axotomized, saline-treated animals (FIG. 3); there was no difference between the V-10,367-treated and vehicle-treated groups, indicating that the effect is non-specific and not due to the compound per se.

Figure 4A:
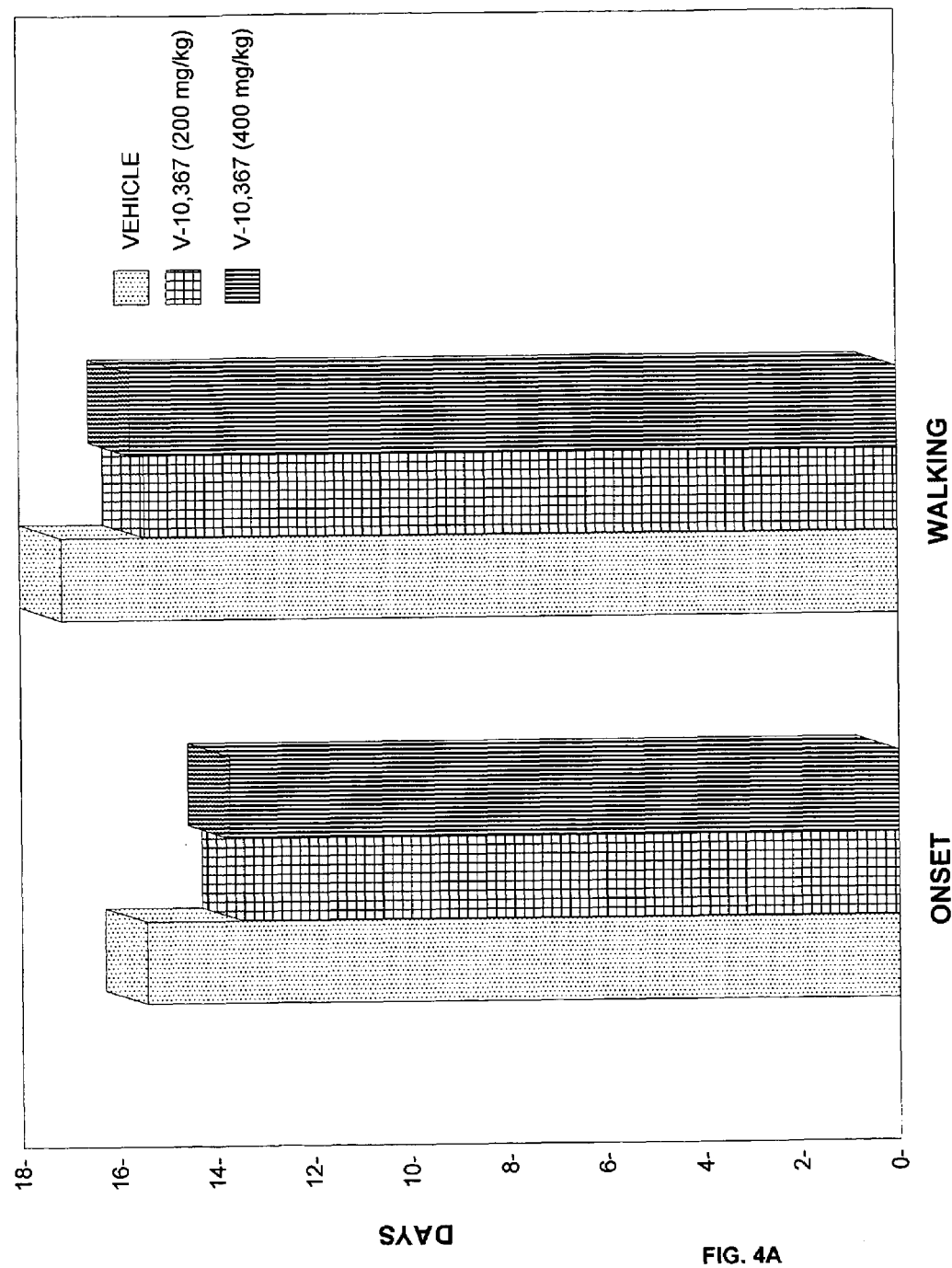
FIG. 4A is a bar graph showing the number of days from axotomy until onset of toe movement and an ability to right the foot ("onset"), and an ability to walk on the hind feet ("walking") in vehicle-treated and rats treated with V-10,367 (200 and 400 mg/kg/day). *p<0.05 (by ANOVA and Fischer's post hoc test).
Figure 4B:
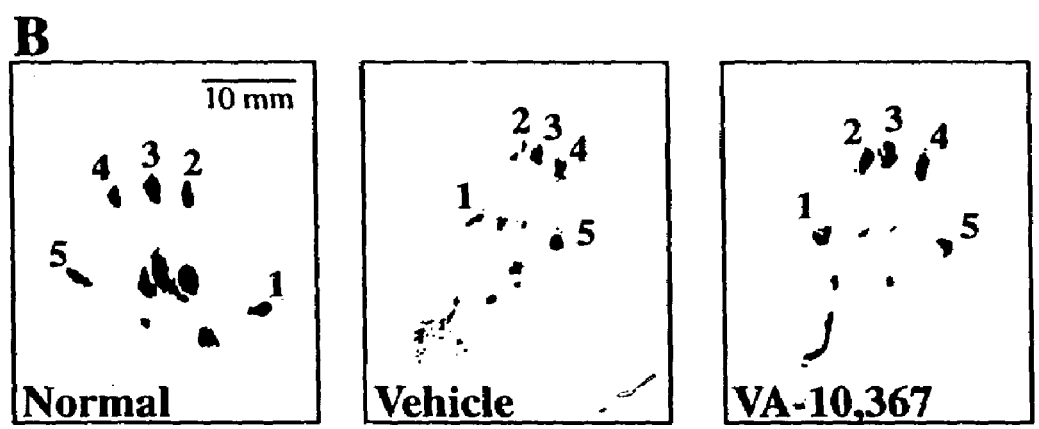
FIG. 4B shows representative foot prints (digits are numbered) at 18 days following unilateral axotomy showing the uninjured (normal) left side from a vehicle-treated rat (left), and from the axotomized side from vehicle-treated (middle) and V-10,367-treated (right) rats. Each image was generated by scanning the original foot print using MacImage (Xerox Imaging Systems, Inc.).

Functional recovery was observed earlier in rats treated with V-10,367 (200 and 400 mg/kg/day) than in rats treated with vehicle only (FIG. 4). The number of days until the animal demonstrated the onset of an abilities to right the foot and move the toes ("onset") and to walk on its hind feet and toes ("walking") were significantly reduced from 15.3±0.33 days (mean±SEM) to 13.7±0.33 days ($p<0.05$; t-statistic (df=4)=3.536) and 16.3±0.33 days to 14±0 days $p<0.0005$; t-statistic (df=4)=7.000), respectively, in the vehicle-treated (n=3) and V-10,367-treated (n=3) animals, respectively (FIG. 4A). Representative foot prints at 18 days following nerve crush are shown in FIG. 4B. The foot print from the non-injured (normal) side of a vehicle-treated animal (left) demonstrates a normal appearance; the animal is able to support its weight on its toes and on the front of its foot while walking, as demonstrated by the lack of a prominent heal imprint. The foot prints on the axotomized side from both vehicle-treated (middle) and V-10,367-treated (right) animals reveal a continued deficit as shown by the heel imprints, although this is less prominent in the foot print from the V-10,367-treated animal. The V-10,367-treated animal also exhibits a greater toe spread compared to the uninjured side. We measured the distance between the first and fifth digits for the animals in each group. This distance was significantly ($p<0.05$; t-statistic (df=4)=3.038) greater in the V-10,367-treated versus the vehicle-treated animals, being 13.0±0.41 mm (n=3) and 11.0±0.58 mm (n=3), respectively; the distance on the uninjured side, combined for both groups, was 19.5±0.39 (n=6).

Figure 5A:
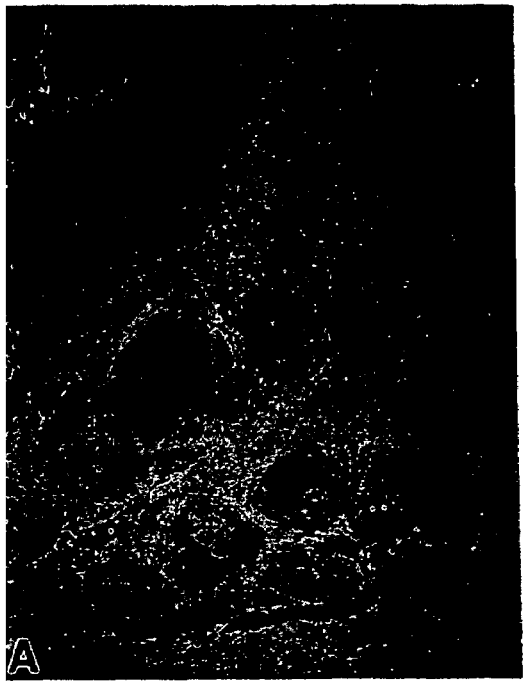
FIGS. 5A-D are electron micrographs of axons in the soleus nerve at 18 days following axotomy from vehicle-treated and V-10,367-treated rats.
Figure 5B:
Figure 5C:
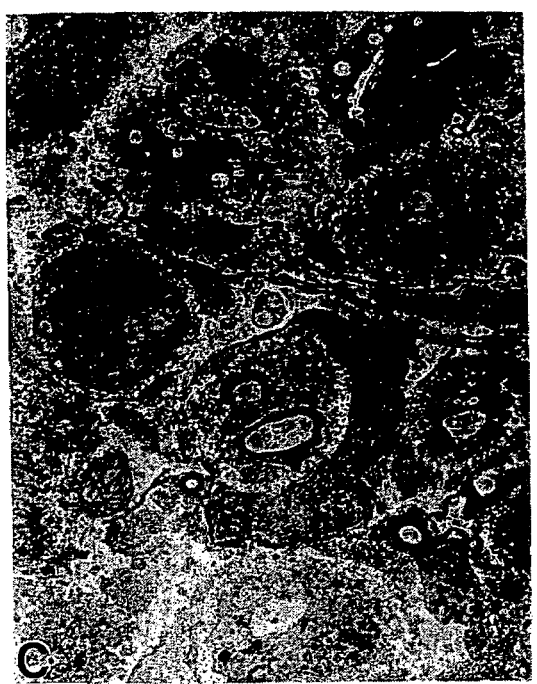
Figure 5D:
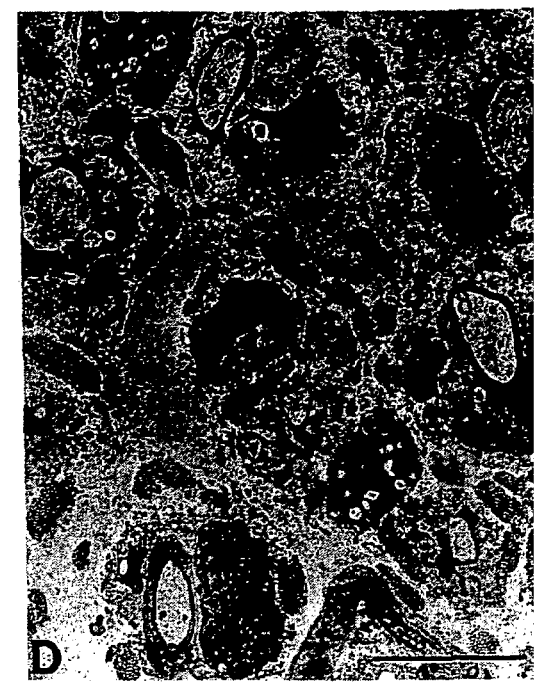
Figure 5E:
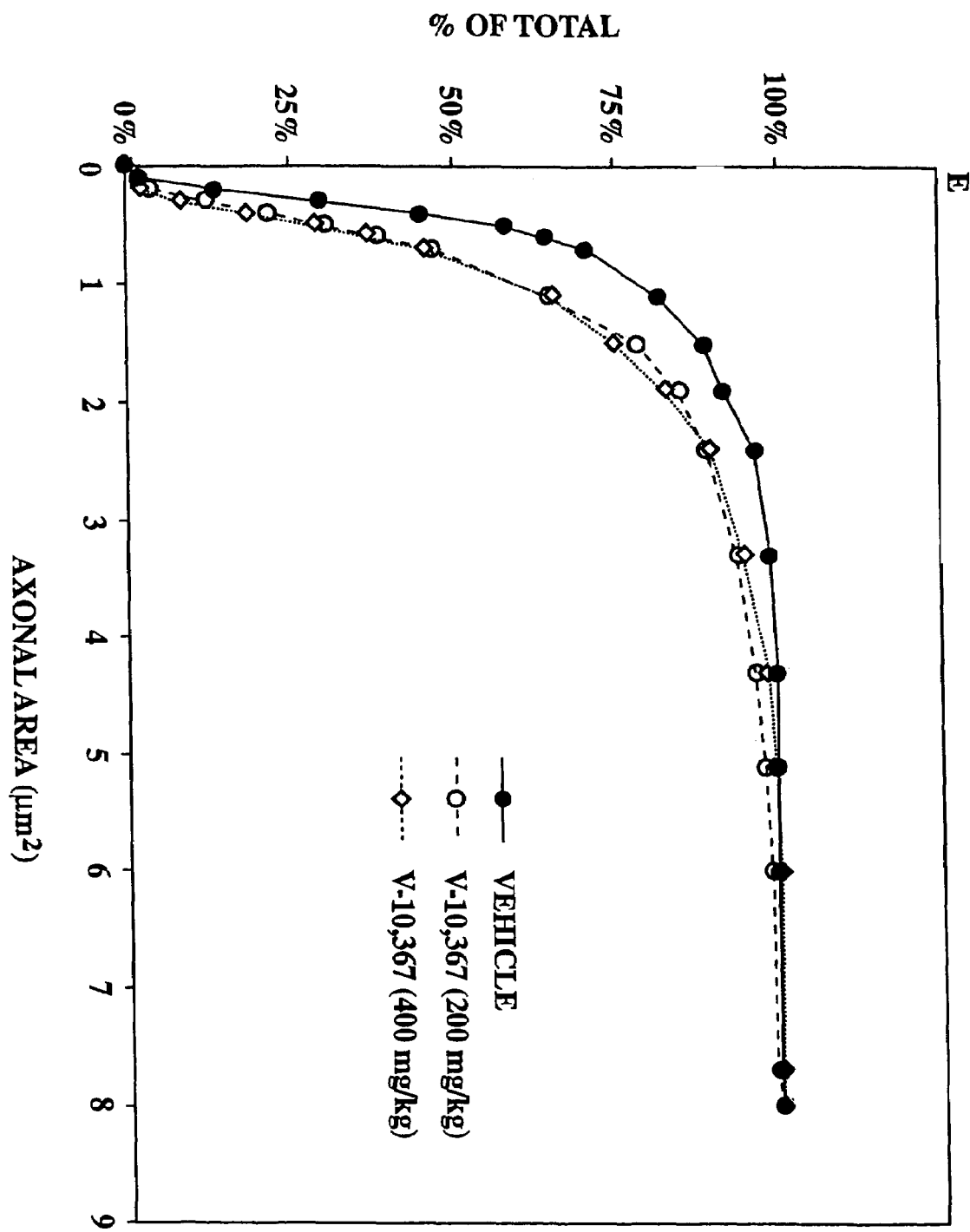
FIG. 5E shows cumulative histograms showing the distribution of axonal areas 18 days after nerve crush demonstrating a shift to the right (indicating larger-sized axons) for axons in the soleus nerve from rats treated with V-10,367 (200 and 400 mg/kg/day). Histograms were constructed from 388, 470, and 472 axons pooled from the three nerves from the vehicle-treated and V-10,367-treated (200 and 400 mg/kg/day) rats, respectively.
Figure 5F:
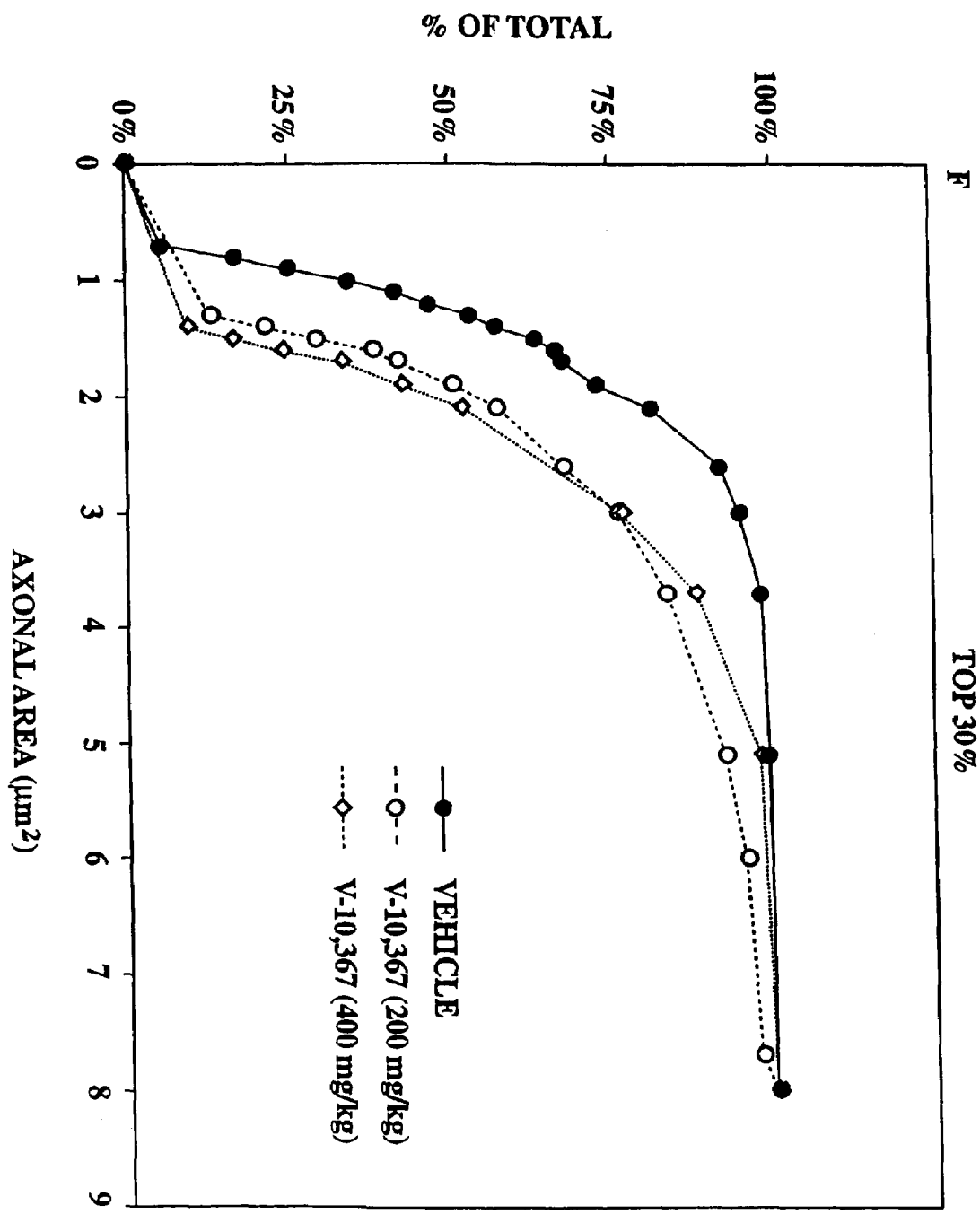
FIG. 5F shows cumulative histograms showing the distribution of the largest 30% of axonal areas. The shift to the right for the V-10,367-treated (200 and 400 mg/kg/day) rats is more pronounced compared to the entire population (E). Histograms were constructed from 116, 141, and 144 axons representing the largest 30% of axons from vehicle-treated and V-10,367-treated (200 and 400 mg/kg/day) rats, respectively.

Morphological examination of the animals was conducted at 18 days following axotomy. Light and electron microscopy revealed that regenerated axons in the sciatic nerve from V-10,367-treated rats exhibited a more advanced stage of maturation compared to vehicle-treated controls. For example, in the soleus nerve, V-10,367-treated rats contain mor myelinated fibers and larger regenerating axons (FIG. 5A-D). This visual impression was confirmed by morphometric analysis of axonal areas in soleus nerve at 18 days after axotomy. Cumulative histograms of axonal areas showed a significant ($p<0.05$; Mann-Whitney U-test) shift to the right for the V-10,367-treated animals, indicating the presence of larger-sized axons (FIG. 5E). Mean axonal areas for the V-10,367-treated animals were increased by 50% compared to vehicle-treated animals; vehicle-treated control values were not different from saline-treated control values obtained previously. Since there are numerous very small regenerating axons, a shift in the distribution of axonal areas could arise from the presence of a smaller proportion of small-caliber axons. To rule out this possibility, we selected for further analysis the largest 30% of axons from each animal. Cumulative histograms for the top 30% of axonal areas demonstrated a significant ($p<0.05$; Mann-Whitney U-test) shift to the right for the V-10,367-treated rats (FIG. 5F), being more dramatic than for the entire population. This analysis reveals that the shift in the distribution of axonal areas for the entire population of axons in the soleus nerve from the V-10,367-treated animals is due to the presence of axons with larger axonal areas.

To test whether different routes of administration are similarly efficacious, we gave rats (two per group) continuous infusion of V-10,367 or vehicle for 18 days via a osmotic minipump. Rates of infusion and concentrations were chosen to produce similar blood levels (approximately 200 ng/mL) as with the subcutaneous injections. Similar results were obtained as those reported above for the subcutaneous injections. V-10,367-treated rats showed earlier functional recovery and larger axonal calibers compared to vehicle-treated controls. However, this route of administration was somewhat less effective, with mean axonal calibers in the soleus nerve being increased by only 40% (compared to the 50% increase produced by daily subcutaneous injections).

Systemic administration of FK506 speeds functional recovery (Gold et al., Restor. Neurol. Neurosci. 6:287-296, 1994) following a nerve-crush lesion by increasing the rate of axonal regeneration (Gold et al., J. Neurosci. 15:7505-7516, 1995) in the sciatic nerve. In marked contrast to FK506, cyclosporin A does not increase nerve regeneration in the rat sciatic nerve following a crush injury. Calcineurin inhibition mediated by cyclophilin A is not necessary or sufficient for promoting nerve regeneration.

Steiner and co-workers (Steiner et al., Nature Medicine 3:1-8, 1997; Steiner et al., Proc. Natl. Acad. Sci. USA 94:2019-2024, 1997) have reported similar findings using FKBP-12 ligands that do not inhibit calcineurin. Topical administration of the FK506 derivative L-685,818 (18-OH, 21-ethyl-FK506) to the nerve crush site was found to accelerate functional recovery (Steiner et al, Nature Medicine 3:1-8, 1997); an increase in axonal calibers and myelinated fibers by light microscopy was found at a distance 2 mm from the crush injury. However, the recent finding that L-685,818-FKBP-12 is able to inhibit calcineurin in C. neoformans (Odom et al., Antimicrob. Agents Chemother. 41:156-161, 1997) makes this compound less attractive for definitively ruling out calcineurin activity in the nervous system. It was further reported (Steiner et al., Nature Medicine 3:1-8, 1997; Steiner et al., Proc. Natl. Acad. Sci. USA 94:2019-2024, 1997) that subcutaneous injections for 18 days of two FKBP-12 ligands that lack the calcineurin-binding structural components of FK506 increase the size of myelinated fibers, again determined at a distance of only 2 mm distal to the crush site; functional recovery was not assessed in animals given these two compounds. It was also shown (Steiner et al., Proc. Natl. Acad. Sci. USA 94:2019-2024, 1997) that an FKBP-12 ligand increases nerve-fiber density in the brain using two toxic chemical-induced models (N-methyl-4-phenyl-1,2,3,6-tetrahydropyridine (MPTP) and 6 hydroxydopamine) of nerve fiber degeneration.

Our study is the first to demonstrate that systemic administration of a potent FKBP-12 ligand that lacks the structural components necessary for calcineurin inhibition speeds functional recovery by accelerating the growth of regenerating axons to the distal musculature following a sciatic nerve-crush lesion. It is possible to separate the nerve regenerative property of FK506 from the immunosuppressant action of FK506-FKBP-12 complexes. Small molecule FKBP ligands lacking immunosuppressant activity are therefore useful as new therapeutic agents for the treatment of human nerve injuries.

TABLE 1

| | | | Mean Neutrite Lengths | | |
|---|---|---|---|---|---|
| | UNTREATED | | | V-10,367 | |
| | CELLS | NGF | 1 nM | 10 nM | 100 nM |
| 96 h | $80 \pm 2.0^1$ (n = 161) | $104 \pm 2.6$ (n = 308) | $110 \pm 2.2$ (n = 65) | $138 \pm 9.4$* (n = 82) | $121 \pm 6.0$* (n = 170) |
| 168 h | $94 \pm 2.4$ (n = 402) | $108 \pm 2.8$ (n = 593) | $136 \pm 5.8^{*,\Delta}$ (n = 98) | $148 \pm 8.6^{*,\dagger\dagger,\Delta}$ (n = 186) | $118 \pm 4.2^{*,\dagger}$ (n = 383) |

[1]Values are mean ± SEM (in μm)
n = number of cells.
*$p < 0.05$, compared to NGF and 1 nM at 96 hours, and NGF at 168 hours (by two-way ANOVA followed by Fisher'post-hoc test).
†$p < 0.05$, compared to 1 nM at 168 hours (by two-way ANOVA followed by Fisher'post-hoc test).
††$p < 0.01$, compared to 100 nM at 168 hours (by two-way ANOVA followed by Fisher'post-hoc test).
Δ$p < 0.05$, compared to their corresponding values at 96 hours (by two-way ANOVA followed by Fisher'post-hoc test).
(All NGF and V-10,367 values are significantly ($p < 0.05$) different from their corresponding untreated control values)

EXAMPLE 2

FK506 Analogs That Do Not Bind FKBP-12 Speed Nerve Regeneration in the Rat Sciatic Nerve The immunosuppressant drug FK506 promotes nerve regeneration in rats following a sciatic nerve lesion in a dose-dependent fashion. Two lines of evidence indicate that the mechanism for the promotion of nerve regeneration is distinct from that producing immunosuppression. First, while the immunosuppressant drugs FK506 and cyclosporin A inhibit T-cell proliferation via a common mechanism, namely calcineurin inhibition following binding to their respective binding proteins, the peptidyl prolyl isomerases FKBP-12 and cyclophilin A, cyclosporin A does not increase nerve regeneration. Second, the potent FKBP-12 inhibitor V-10,367, which lacks the structural components of FK506 that are required for calcineurin inhibition also speeds nerve regeneration. Thus, the immunosuppressant and nerve regenerative properties of FKBP-12 ligands are separable, the latter activity not involving calcineurin inhibition.

A variety of FKBP ligands with different FKBP-12 binding potencies increase neurite outgrowth in SH-SY5Y cells and speed nerve regeneration in the sciatic nerve crush model. Surprisingly, overall efficacy of the compounds V-12,338, V-12,339, and V-12,559 (which is the same as V-13,670) (Vertex Pharmaceuticals Incorporated, Cambridge, Mass.) on neurite outgrowth, determined by measuring neurite length, did not correlate with the ability of the compounds to inhibit FKBP-12. Two compounds exhibit the greatest effect on neurite lengths, V-12,338 and V-12,339. V-12,338 is a potent FKBP-12 inhibitor and V-12,339 is a non-inhibitor. Rats given daily subcutaneous injections of V-12,559, which does not bind FKBP-12, showed earlier functional recovery and more advanced regeneration (larger axonal calibers, more myelinated fibers distal to the crush site) compared to V-12,367-treated rats at equivalent dosages. Both compounds are effective upon oral (gavage) administration.

These results indicate either that the compounds increase neurite outgrowth and nerve regeneration via a mechanism that does not involve FKBP-12, or that multiple FKBPs (including FKBP-12) are involved.

This invention has been detailed both by example and by direct description. It should be apparent that one having ordinary skill in the relevant art would be able to surmise equivalents to the invention as described in the claims which follow but which would be within the spirit of the foregoing description. Those equivalents are to be included within the scope of this invention.

I claim:

1. A method of identifying a FK506 analog that stimulates nerve cell growth, the method comprising:
    screening a plurality of FK506 analogs for binding to FKBP-12 and for rotamase activity; and
    selecting a FK506 analog of interest that binds FKBP-12 with a $K_d$ of at least 10 μM without inhibition of FKBP-12 rotamase activity;
    thereby identifying a FK506 analog that stimulates nerve growth.

2. the method of claim 1, further comprising assaying the FK506 analog for activity in promoting nerve cell growth.

3. The method of claim 2, wherein the assay for activity in promoting nerve cell growth comprises exposing a cell to the selected FK506 analog and determining if neurite outgrowth is promoted.

4. The method of claim 3, wherein the cell is a neuroblastoma cell.

5. The method of claim 3, wherein the cell is a sciatic nerve cell.

6. The method of claim 1, wherein the FK506 analog binds FKBP-12 with a $K_d$ of at least 30 μM.

7. The method of claim 1, wherein the FK506 analog binds FKBP-12 with a $K_d$ of at least 100 μM.

8. A method of identifying a FK506 analog that stimulates nerve cell growth, the method comprising:
    screening FK506 analogs for binding to FKBP-12 in vitro;
    selecting one or more FK506 analogs of interest that bind FKBP-12 with a $K_d$ of at least 10 1 μM without inhibition of rotamase activity, wherein the one or more FK506 analogs of interest do not inhibit FKB-12 rotamase activity in vivo when administered to a patient at a dosage level up to about 100 mg/kg body weight/day; and
    determining if the one or more FK506 analogs of interest promotes nerve cell growth in an assay for nerve cell growth, wherein the assay for nerve cell growth is an in vivo or an in vitro assay.

9. The method of claim 8, wherein the assay for nerve cell growth comprises exposing a cell to the one or more FK506 analogs of interest in vitro and determining if neurite outgrowth is promoted.

10. The method of claim 9, wherein the cell is a neuroblastoma cell.

11. The method of claim 9, wherein the FK506 analog binds FKBP-12 with a $K_d$ of at least 30 μM.

12. The method of claim 9, wherein the FK506 analog binds FKBP-12 with a $K_d$ of at least 100 μM.

13. The method of claim 8, wherein the assay for nerve cell growth comprises exposing a sciatic nerve cell to the one or more FK506 analogs of interest.

14. The method of claim 8, wherein the assay for nerve cell growth is an in vivo assay.

* * * * *